(12) United States Patent
Rose et al.

(10) Patent No.: US 7,312,191 B2
(45) Date of Patent: Dec. 25, 2007

(54) CONJUGATED NITRO ALKENE ANTICANCER AGENTS BASED ON ISOPRENOID METABOLISM

(75) Inventors: Seth D. Rose, Tempe, AZ (US); Karl J. Okolotowicz, Goleta, CA (US); Rosemarie F. Hartman, Tempe, AZ (US); Jason Houtchens, Tempe, AZ (US)

(73) Assignee: Arizona Biomedical Research Commission, Phoenix, AZ (US)

( * ) Notice: Subject to any disclaimer, the term of this patent is extended or adjusted under 35 U.S.C. 154(b) by 0 days.

(21) Appl. No.: 10/901,082

(22) Filed: Jul. 29, 2004

(65) Prior Publication Data

US 2005/0026812 A1 Feb. 3, 2005

Related U.S. Application Data

(60) Provisional application No. 60/490,444, filed on Jul. 29, 2003.

(51) Int. Cl.
*A61K 38/00* (2006.01)
*C07C 201/00* (2006.01)
*C07D 207/08* (2006.01)

(52) U.S. Cl. .................. 514/2; 568/945; 530/300; 548/567

(58) Field of Classification Search .............. 514/18
See application file for complete search history.

(56) References Cited

U.S. PATENT DOCUMENTS 5,595,756 A * 1/1997 Bally et al. ............ 424/450
6,166,082 A 12/2000 Kluender et al.

FOREIGN PATENT DOCUMENTS

WO      WO 93/01824      2/1993

OTHER PUBLICATIONS

Gura, T., "Systems for Identifying New Drugs are Often Faulty," Science (1997), vol. 278, pp. 1041-1042.*
Montagnier et al Activites Cytotoxique Et Antitumorale Des Beta-Nitrostyrenes, Chimie Therapeutique, Editions Dimeo, Arcueil, Fr, vol. 6, No. 3, 1971, pp. 186-191.*
Okolotowicz et al, "Inactivation of Protein Farnesyltransferase by Active-Site-Targeted Dicarbonyl Compounds," Arch. Pharm. Med. Chem.(2001), vol. 334, pp. 194-202.*
Montagnier et al Activites Cytotoxique Et Antitumorale Des Beta-Nitrostyrenes, Chimie Therapeutique, Editions Dimeo, Arcueil, Fr, vol. 6, No. 3, 1971 ,pp. 186-191.*
Bergo M.O., et al, "On the physiological importance of endoproteolysis of CAAX proteins: heart-specific RCE1 knockout mice develop a lethal cardiomyopathy," J Biol Chem. Feb. 6, 2004;279(6):4729-36. Epub Nov. 18, 2003.*
Montagnier et al Activites Cytotoxique Et Antitumorale Des Beta-Nitrostyrenes, Chimie Therapeutique, Editions Dimeo, Arcueil, Fr, vol. 6, No. 3, 1971, pp. 186-191, demonstrates a number of compounds used in vivo and in vitro.*
http://en.wikipedia.org/wiki/In_vivo.*
Organic Chemistry, 5th Ed. Morris & Boyd, p. 1205.*
Montagnier et al Activites Cytotoxique Et Antitumorale Des Beta-Nitrostyrenes, Chimie Therapeutique, Editions Dimeo, Arcueil, Fr, vol. 6, No. 3, 1971, pp. 186-191., of record in IDS.*
Kabalka and Varma, *Organic Preparations and Procedures International* 1987, 19, 283-328.
The Merck Index Named Reactions, 182. Henry Reaction.
Nasr, et al., *Advances in Pharmacology and Chemotherapy* 1984, 20, 123-190.
Abstract of Cassels, et al., *Anales de la Asociacion Quimica Argentina* 1982, 70, 283-8.
Yuen and Cheng, *J. Med. Chem.* 1969, 12, 157-161.
Alston, et al., *Biooganic Chemistry* 1985, 13, 375-403.
Alston, et al., *Acc. Chem. Res.* 1983, 16, 418-424.
Fujii, Masayuki, "A Highly Chemoselective Reduction of Conjugated Nitro Olefins with Hantzsch Ester in the Presence of Silica Gel", Bulletin of the Chemical Society of Japan,vol. 61(11), pp. 4029-4035 (1988).
Knight, John et al., "A New Acylative Cycoaddition Reaction", Journal of the Chemical Society, Perkin Trans. I: Organic and Bio-Organic Chemistry (1972-1999), pp. 979-984 (1989).
Knight, John et al., "A New Acylative Cycloaddition Reaction", Journal of the Chemical Society, Chemical Communications, pp. 189-190 (1987).
Knochel, Paul, et al., "Dehydration of Nitroaldols with Dicyclohexylcarbodiimide: Preparation of Nitroolefins under Mild Conditions" Synthesis, pp. 1017-1018 (1982).
Bezbarua, Maitreyee S., et al., "A Facile Procedure for the Conversion of Nitroolefins to Carbonyl Compounds using the Al-NiCl2*6H2O-THF System", Chemistry Letters, pp. 325-326 (1999).
Saikia, Anil K., et al., The Zinc-Trifluoroacetic Acid Reaction in Organic Solvents: A Facile Procedure for the Conversion of Nitroolefins into Carbonyl Compounds under Mild Conditions, Journal of Chemical Research, Synopses, pp. 124-125 (1996).
Saikia, Anil K., et al., "An Improved Synethsis of Conjugated Nitroolefins", Synthesis, pp. 685-686 (1994).

(Continued)

Primary Examiner—Anish Gupta
Assistant Examiner—Thomas S. Heard
(74) Attorney, Agent, or Firm—Banner & Witcoff, Ltd.

(57) ABSTRACT

Conjugated nitro alkene compounds hamper or prevent proliferation of cancer cells in cell culture and in cancer patients, which can result in a decrease in tumor size and/or disappearance of the cancer. The compounds may act by interference with cancer cell biochemistry, in which isoprenoid groups such as farnesyl and geranylgeranyl become bonded to various oncogenic proteins such as Ras, RhoA, RhoB, or some other growth-related cellular protein(s).

6 Claims, No Drawings

OTHER PUBLICATIONS

Montagnier, L. et al., "Activities Cytotoxique Et Antitumorale Des Beta-Nitrostytenes," Chimie Therapeutique, Editions Dimeo, Arcueil, Fr. vol. 6, No. 3, 1971, pp. 186-191.

Okolotowicz, Karl J., et al., "Inactivation of Protein Farnesyltransferase by Active-Site-Targeted Dicarbonyl Compounds," Arch. Pharm. Pharm. Med. Chem., vol. 334, 2001, pp. 194-202.

Cassels, et al., *Anales de la Asociacion Quimica Argentina* 1982, 70, 283-8.

* cited by examiner

CONJUGATED NITRO ALKENE ANTICANCER AGENTS BASED ON ISOPRENOID METABOLISM

CROSS REFERENCE TO RELATED APPLICATION

This application claims benefit under 35 U.S.C. § 119(e) to U.S. provisional Application No. 60/490,444, filed Jul. 29, 2003, the disclosure of which is hereby incorporated by reference in its entirety.

FIELD OF THE INVENTION

The present invention is directed to pharmaceutical compounds and, more particularly, to conjugated nitro alkene compounds and methods of administering the compounds for the treatment of cancer.

DESCRIPTION OF RELATED ART

At least three enzymes are believed to be responsible for the prenylation of cell division proteins: farnesyltransferase and geranylgeranyltransferases I and II. Consequently, various inhibitors of these enzymes are known and prevent protein prenylation in vivo, inhibiting tumor cell growth and/or reverting tumor cells to a normal phenotype. A disadvantage associated with many of these inhibitors is that the active site of the prenylation enzyme is blocked only reversibly through competitive inhibition processes, which allows buildup of unused substrates to reverse the inhibition competitively and allows multi-drug resistance proteins to reverse the inhibition by pumping the inhibitors out of the cancer cell.

SUMMARY OF INVENTION

The present invention is directed to nitro alkene compounds which hamper or prevent the proliferation of cancer cells in cell culture and in cancer patients, which can result in a decrease in tumor size and/or disappearance of the cancer. The compounds may act by interference with cancer cell biochemistry, in which isoprenoid groups such as farnesyl and geranylgeranyl become bonded to various oncogenic proteins such as Ras, RhoA, RhoB, or some other growth-related cellular protein(s), in a process referred to as prenylation. Attachment of the isoprenoid group to the aforementioned proteins, collectively referred to hereinafter as cell division proteins (CDPs), is a key prerequisite for the functioning of these proteins in cell division. For instance, the farnesylation of Ras is required for the proper subcellular localization of Ras to lipid bilayers in membranes within the cell, where it recruits the protein kinase Raf. Raf thereupon becomes activated and initiates a phosphorylation cascade that results in gene expression that induces cell division. Likewise, RhoA requires geranylgeranylation for activation of cell division. The prenylation of proteins requisite for cancer cell division is quite complex, as in the case of RhoB, where the ratio of farnesylation to geranylgeranylation appears to be key to the proper partitioning of RhoB between various subcellular locations, an imbalance being associated with transformation of the cell to a tumor phenotype.

Compounds of the present invention inhibit cancer cell growth, possibly by interfering with farnesylation and/or geranylgeranylation of CDPs and/or by altering the farnesylation:geranylgeranylation ratio of CDPs, through interaction with one or more prenylation enzymes in tumor cells. The nature of the interaction of compounds of the invention with prenylation enzymes is designed to be through covalent bond formation by chemical reaction of nucleophilic side chains of the enzyme's component amino acids with the highly electrophilic carbon-carbon double bond conjugated to the nitro group of the conjugated nitro alkene system of Formula (I). Irreversible or slowly reversible interference of prenylation enzyme activity by covalent bond formation, preferably in the active site of the prenylation enzyme, may be advantageous over the current therapeutic practice of reversible inhibition of the prenylation enzymes, due to the aforementioned multidrug resistance mechanisms of tumor cells. Additional specific potential advantages associated with this invention over reversible inhibitors of prenyltransferases are: (1) buildup in the cellular concentration of unused substrates (e.g., farnesyl diphosphate, Ras and Rho proteins) cannot reverse the covalent binding of the compounds of this invention in the way reversible inhibitors can be displaced by competition of unused substrates, making the compounds of this invention more effective; (2) periodic dosing of compounds of this invention may be used to adjust the activity level of the enzyme even in the absence of the drug, a potential benefit of which may be decreased toxic side effects in the patient; and (3) periodic dosing of compounds of this invention, in contrast to the need for the constant presence of reversible inhibitors for their effectiveness, may minimize the cancer cell's ability to become resistant to the therapy.

Several embodiments of the invention are defined below and are directed to various aspects of the invention. None of these embodiments should be construed as limited by any theory or by any biological or chemical property, mechanism, or mode of interaction.

In one embodiment, the present invention is a compound of Formula (I)

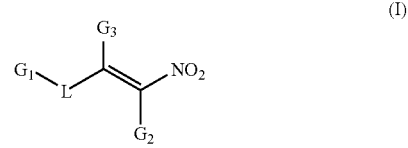

(I)

or pharmaceutically acceptable salt, ester, or prodrug thereof, wherein:

$G_1$ is selected from the group consisting of alkyl, haloalkyl, alkoxy, alkylthio (and the sulfoxide and sulfone derivatives thereof), alkenyl, cycloalkyl, cycloalkoxy, aryl, aralkyl, aryloxy, heterocyclo, a hydrophobic group, a substrate-mimicking isoprenoid, a polypeptide, a peptidomimetic group, and combinations thereof;

$G_2$ is a hydrogen atom or a substituent as defined for $G_1$;

$G_3$ is a hydrogen atom or a substituent as defined for $G_1$; and

L is a linker selected from the group consisting of a bond, alkyl, alkenyl, alkynyl, aryl, and aralkyl.

In another embodiment, if the linker L is a bond and $G_2$ is a hydrogen atom, the invention is a compound of the Formula (Ia):

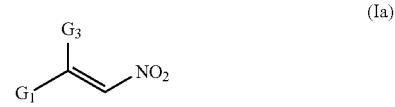

(Ia)

or pharmaceutically acceptable salt, ester, or prodrug thereof, wherein:

$G_1$ and $G_3$ are as defined above.

In another embodiment, if the linker L is a bond and $G_3$ is a hydrogen atom, the invention is a compound of the Formula (Ib):

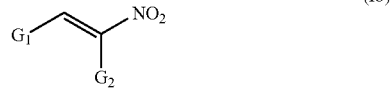

or pharmaceutically acceptable salt, ester, or prodrug thereof, wherein:

$G_1$ and $G_2$ are as defined above.

In another embodiment, if the linker is a bond and $G_2$ and $G_3$ are each a hydrogen atom, the resulting compound is of the Formula (Ic):

In a preferred embodiment, the present invention is a compound of Formula (I) wherein $G_1$ is a branched alkenyl, preferably farnesyl or geranylgeranyl, or partially saturated derivatives thereof. In another preferred embodiment, $G_1$ is a polypeptide, or a peptidomimetic of a polypeptide, that comprises at least one cysteine, and preferably comprises the polypeptide sequence Cys-a-a-X, wherein a is an amino acid having an aliphatic side chain and wherein X is selected from the group consisting of methionine, glutamine, serine, alanine, leucine, and phenylalanine.

In another preferred embodiment, the present invention is a compound of Formula (I) wherein $G_2$ is a hydrogen atom, methyl, or a polypeptide that comprises at least one cysteine, and preferably comprises the polypeptide sequence Cys-a-a-X, wherein a is an amino acid having an aliphatic side chain and wherein X is selected from the group consisting of methionine, glutamine, serine, alanine, leucine, and phenylalanine. Alternatively, $G_2$ may be a peptidomimetic of such a polypeptide.

In another preferred embodiment, the present invention is a compound of Formula (I) wherein $G_3$ is a hydrogen atom, methyl, or a polypeptide that comprises at least one cysteine, and preferably comprises the polypeptide sequence Cys-a-a-X, wherein a is an amino acid having an aliphatic side chain and wherein X is selected from the group consisting of methionine, glutamine, serine, alanine, leucine, and phenylalanine. Alternatively, $G_3$ may be a peptidomimetic of such a polypeptide.

In another embodiment, the present invention is a pharmaceutical composition comprising a compound of Formula (I) and a pharmaceutically acceptable carrier.

In another embodiment, the present invention is a method of inhibiting the proliferation of cancer cells, inhibiting tumor growth, or reverting tumor cells to a normal phenotype in a patient, the method comprising administration of an effective amount of a compound of Formula (I).

In another embodiment, the present invention is a method of inhibiting a CDP-prenylation enzyme in a patient, the method comprising administration of an effective amount of a compound of Formula (I). In a preferred embodiment of this method, the CDP prenylation enzyme is selected from the group consisting of protein farnesyltransferase, protein geranylgeranyltransferase I, and protein geranylgeranyltransferase II. In another preferred embodiment of this method, a terminal portion of the compound comprises an electrophilic conjugated nitro alkene moiety and the CDP prenylation enzyme comprises at least one amino acid having a nucleophilic side chain that interacts with the electrophilic nitro alkene moiety to form a covalent bond therewith and inhibit CDP prenylation enzyme activity.

In another embodiment, the present invention is a method of preventing the prenylation of a CDP in a patient, the method comprising administration of a compound of Formula (I) having a terminal portion of the compound comprising an electrophilic conjugated nitro alkene moiety, wherein the CDP comprises at least one nucleophilic cysteine sulfhydryl group that interacts with the conjugated nitro alkene moiety to prevent or decrease CDP prenylation by forming a derivative of the CDP that is biologically inactive or less active for cell division than the corresponding prenylated CDP.

In another embodiment, the present invention is a method for the treatment or prevention of cancer in a patient in need of such treatment or prevention, the method comprising the administration of an effective amount of a compound of Formula (I) to the patient.

In preferred embodiments, the invention is any of the above methods wherein the patient is a mammal, preferably a human.

DETAILED DESCRIPTION OF THE PREFERRED EMBODIMENTS

Interference with prenylation of cell division proteins has the potential to alter the subcellular distribution of the proteins, thereby interfering with the biochemical processes that lead to unrestrained cell division of the tumor cell. Possible consequences of this interference are cancer cell death and/or reversion to a normal phenotype, as observed with reversible inhibitors of farnesyltransferase, hereinafter referred to as conventional farnesyltransferase inhibitors or conventional FTIs.

The prenylation enzymes that attach the farnesyl or geranylgeranyl group to CDPs use an isoprenoid substrate and the CDP as a substrate. The isoprenoid portion of this substrate becomes transferred to the CDP by loss of inorganic pyrophosphate, thereby producing a prenylated-CDP, in a chemical reaction summarized by equation (1) below:

wherein E represents a protein prenylation enzyme, examples of which are protein farnesyltransferase (FTase) and protein geranylgeranyltransferases (GGTases). In the case of FTase, the substrate isoprenoid diphosphate is farnesyl diphosphate, also known as farnesyl pyrophosphate. In the case of GGTases, the isoprenoid substrate is geranylgeranyl diphosphate, also known as geranylgeranyl pyrophosphate. The former enzyme produces a farnesylated CDP, whereas the latter enzymes produce a geranylgeranylated CDP.

Because normal cells also require FTase and GGTase activity, the optimal regulation of prenyltransferase activity must be determined empirically.

To confer covalent bonding reactivity toward the prenylation enzyme, we have incorporated into compounds of Formula (I) an electrophilic group comprising the conjugated nitro alkene functionality, shown below:

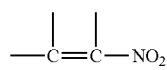

which is often formulated to be a resonance hybrid of the following canonical structures:

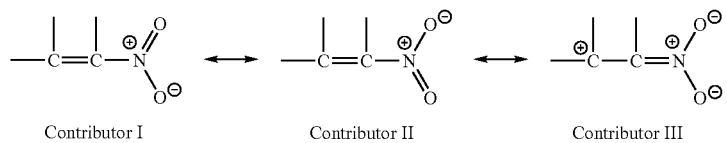

Contributor I          Contributor II          Contributor III

The resonance form designated Contributor III is formally indicative of the carbon-carbon double bond being in conjugation with the attached nitro group, and it clearly shows the electrophilic character of the carbon atom β to the nitro group, i.e., the one with the formal positive charge. Consequently, the conjugated nitro alkene moiety is capable of readily reacting with nucleophiles (e.g., $Nu^-$, $Nu^-H^+$, Nu-H) in an addition reaction to produce a covalent adduct, shown below in equation (2):

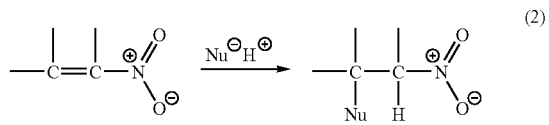

Relevant to the instant disclosure, the active sites of prenylation enzymes have amino acid side chains that are nucleophilic. Examples of common amino acids with nucleophilic side chains are cysteine, lysine, hydroxylysine, tyrosine, histidine, arginine, serine, threonine, aspartic acid, and glutamic acid. FTase, for example, bears several nucleophilic groups in the active site, such as Lys 294β, Lys 164α, His 248β, Tyr 300β, and Arg 291β, among others. Upon noncovalent binding of a conjugated nitro alkene of Formula (I) to FTase, a nucleophilic side chain of an active site amino acid could undergo the addition reaction summarized by equation (2) shown hereinabove. The chemical reaction between the conjugated nitro alkene and the prenylation enzyme would result in changes in the active site of the prenylation enzyme, producing a modified enzyme of reduced catalytic ability, due to blockage of access of the natural substrate(s) to the active site, chemical modification of a key catalytic group in the active site with concomitant reduction of catalytic power, or other means. In principle, this chemical modification through covalent bonding can be irreversible or nearly irreversible (e.g., slowly reversible) due to covalent bonding between the conjugated nitro alkene and the prenylation enzyme.

The function of the portion of Formula (I) represented by $G_1$, and potentially by $G_2$ and $G_3$, is to aid in the selectivity of the compounds of Formula (I) for prenylation enzymes and to aid in high-affinity, noncovalent binding of the compound of Formula (I) to the prenylation enzyme prior to the covalent bonding reaction between the enzyme and the inhibitor.

Typically, enzyme inhibitors structurally mimic a natural substrate of an enzyme. This structural similarity between substrate and inhibitor provides the intermolecular interactions (electrostatic, hydrogen-bonding, hydrophobic, etc.) between inhibitor and enzyme needed, for example, to efficiently block the binding of substrate by the enzyme or to induce a conformational change in the enzyme that reduces the enzyme's catalytic efficiency. The structural similarity between substrate and inhibitor also serves to confer specificity on the inhibitor for a particular enzyme or enzymes. This minimizes the effect of the agent on various essential biochemical processes, e.g., basic metabolic processes in normal cells, that are not the targets of the anticancer strategy, resulting in the benefit of optimal therapeutic action versus undesirable toxicity toward normal cells or the patient systemically.

To achieve specificity of the conjugated nitro alkenes for the active site of a prenylation enzyme, so as to optimally interfere with the prenylation of CDPs in cancer cells, structural features of the natural substrate(s) of the prenylation enzyme may be incorporated into groups $G_1$, $G_2$, and $G_3$ of compounds of Formula (I). One of the substrates of the prenylation enzyme is an isoprenoid diphosphate, as indicated in equation (1) shown hereinabove. Another substrate is a CDP, which typically has a carboxyl terminal amino acid recognition sequence summarized as Cys-a-a-X, where Cys represents cysteine, a represents an amino acid with an aliphatic side chain, and X represents methionine, glutamine, serine, or alanine for FTase specificity, or alternatively, leucine or phenylalanine for GGTase I specificity. Known recognition sequences of geranylgeranyltransferase II are Cys-Cys-b-b, Cys-b-Cys, and Cys-Cys, where b is any amino acid. Thus, groups $G_1$, $G_2$, and/or $G_3$ may advantageously comprise a substrate-mimicking isoprenoid or other hydrophobic group, a substrate-mimicking peptidic or peptidomimetic group, or a combination of these features.

Compounds of Formula (I) have the capability to covalently bond to prenylation enzymes. As described in equation (2) shown hereinabove, the carbon-carbon double bond in conjugation with the $NO_2$ group serves as an electrophile for covalent bonding to an enzyme-active-site nucleophilic group. The altered enzyme molecule with the active site modified by the attachment of the compound of Formula (I) has reduced activity. Thus, compounds of Formula (I) regulate the level of activity of the prenyltransferase. The compounds may do so by hampering access of the natural substrates to the active site, by altering the catalytic ability of active site residues, and/or other mechanisms (e.g., inducing conformational changes in the prenyltransferase that affect its catalytic ability). The regulation of the biochemical level of prenylation catalytic activity in the cell may also be achieved by complete inhibition of a portion of the prenyltransferase molecules while leaving some molecules completely unmodified.

A further way in which compounds of this invention might function to regulate protein prenylation in cancer cells to the benefit of cancer patients is by prenylation-enzyme-mediated covalent bonding of the conjugated nitro alkenes to the nucleophilic group of the CDP that is normally prenylated. In other words, the prenylation enzyme might catalyze the attachment of the conjugated nitro alkene to the nucleophilic cysteine sulfhydryl group in the Cys-a-a-X recognition sequence of the CDP that is normally prenylated in the cancer cell, resulting in the aberrant attachment of the conjugated nitro alkene to the CDP and a concomitant loss of function of the CDP in cancer cell proliferation.

As $G_1$, $G_2$, and $G_3$ (in the case that L is a bond, a lower alkyl or a conjugated $\pi$ system) can influence the electrophilicity of the nitro alkene functionality through electronic effects (e.g., inductive and resonance) and/or steric effects, a further function of $G_1$, $G_2$, and $G_3$ is to modify the reactivity of the nitro alkene functionality for optimal reactivity with the aforementioned nucleophiles to achieve the most desirable therapeutic effect. For example, electron-withdrawing groups enhance the reactivity of the nitroalkene functionality, electron-donating groups reduce the reactivity, and bulky groups reduce the reactivity through steric effects that hamper the approach of the nucleophile. In this regard, preferred embodiments employ alkyl and haloalkyl substituents for $G_1$, $G_2$, and $G_3$.

The function of the linker portion represented by L in Formula (I) is to serve as a chemical linkage between the portions $G_1$ and the terminal conjugated nitro alkene portion of the molecule. This linkage may be accomplished simply by a single bond. Otherwise, L may comprise a single atom or a series of bonded atoms that confer flexibility on the molecule so that $G_1$ and possibly also $G_2$ and $G_3$ may optimally function in their respective manners, or L may comprise a single atom or a series of bonded atoms that confer the proper distance relationship between $G_1$ and the conjugated nitro alkene portion of the molecule or between $G_1$, $G_2$, and $G_3$ so that $G_1$ and possibly also $G_2$ and $G_3$ may optimally function in their respective manners, including the conferring of specificity of compounds of Formula (I) on particular prenylation enzymes.

One preferred embodiment of the invention is a compound of Formula (I), having at least one carbon-carbon double bond in conjugation with an attached nitro group (NO$_2$), in which the group $G_1$ is an isoprenoid group or an analogue of an isoprenoid group known or expected to bind preferentially to a prenylation enzyme and L is a suitable linker. To optimize the specific structure of such a compound for noncovalent binding to and covalent reactivity with a prenylation enzyme, variation of the distance between the covalent-bonding conjugated nitro alkene portion of the molecule and the farnesyl-mimicking or geranylgeranyl-mimicking portion ($G_1$) of the molecule can be achieved through variation of the structure of the linker L, e.g., by alteration of the length of the linker in the generalized structural formula below, where, for example, n may represent 0 to 10 carbon atoms.

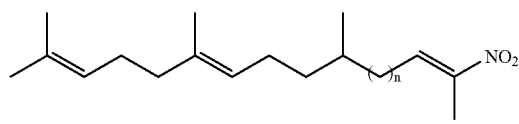

Targeted for FTase

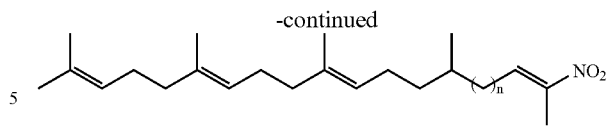

Targeted for GGTase

Based on the above considerations, specific embodiments of this invention include the following examples of compounds specified by Formula (I), although many modifications to achieve the desired effect are readily apparent to those skilled in the art, having regard for this disclosure:

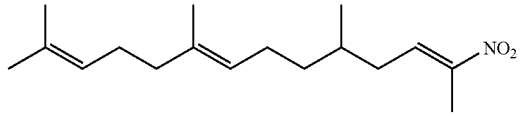

5,9,13-Trimethyl-2-nitrotetradeca-2,18,12-triene (RG-4)

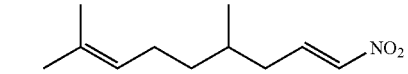

4,8-Dimethyl-1-nitronona-1,7-diene (RG-7)

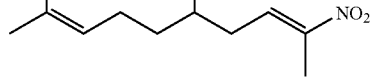

5,9-Dimethyl-2-nitrodeca-2,8-diene (RG-14)

Compound RG-4 at a concentration of 50 µM was found to inhibit FTase to the extent of 83% after a 30-minute treatment in vitro. At a concentration of 5 µM, it decreased FTase activity by 35%. Thus, exposure of FTase to RG-4 for 30 minutes resulted in a decrease in FTase activity to levels that were dependent on the concentration of RG-4, thus exemplifying the ability of RG-4 to regulate prenylation activity in vitro.

The compound RG-4 was also found to be highly active against several types of human cancer cells grown in culture. In Table 1 the concentration of the compound required for 50% growth inhibition (GI$_{50}$) of the specified human cancer cells is displayed.

Likewise, compound RG-7 was effective at inhibiting the growth of human cancer cells in culture. The GI$_{50}$ values of this compound against specified human cancer cells grown in culture are shown in Table 1.

TABLE 1

Conjugated Nitro Alkene Cell Culture Data

| Human cancer cell line | GI$_{50}$/molar for RG-4 | GI$_{50}$/molar for RG-7 |
| --- | --- | --- |
| Colon (HT-29) | $10^{-4}$ to $10^{-5}$ | $10^{-4}$ to $10^{-5}$ |
| Colorectal (Colo-205) | $10^{-4}$ to $10^{-5}$ | $10^{-4}$ to $10^{-5}$ |
| NSC Lung (H-460) | $1.1 \times 10^{-5}$ | $1.2 \times 10^{-5}$ |
| Prostate (PC-3) | $1.5 \times 10^{-6}$ | $4.4 \times 10^{-5}$ |
| Acute myeloid leukemia (HL-60) | $10^{-6}$ to $10^{-7}$ | $>10^{-4}$ |
| Fibrosarcoma (HT-1080) | $10^{-6}$ to $10^{-7}$ | $10^{-4}$ to $10^{-5}$ |
| Urinary bladder (T-24) | $10^{-4}$ to $10^{-5}$ | $10^{-4}$ to $10^{-5}$ |
| Colon (Caco-2) | $10^{-4}$ to $10^{-5}$ | $>10^{-4}$ |

Compound RG-14 was also effective at inhibiting the growth of human cancer cells in culture. The $GI_{50}$ values of this compound against specified human cancer cells and mouse leukemia cells grown in culture are shown in Table 2.

TABLE 2

Conjugated Nitro Alkene Cell Culture Data

| Human cancer cell line | $GI_{50}$/molar for RG-14 | $GI_{50}$/molar for SRG-8 |
| --- | --- | --- |
| Pancreatic (BXPC-3) | $62 \times 10^{-6}$ | $>47 \times 10^{-6}$ |
| Breast (MCF-7) | $39 \times 10^{-6}$ | $>47 \times 10^{-6}$ |
| Central nervous system (SF268) | $73 \times 10^{-6}$ | $>47 \times 10^{-6}$ |
| Lung (NCI-H460) | $72 \times 10^{-6}$ | $>47 \times 10^{-6}$ |
| Colon (KM20L2) | $77 \times 10^{-6}$ | $>47 \times 10^{-6}$ |
| Prostate (DU-145) | $72 \times 10^{-6}$ | $>47 \times 10^{-6}$ |
| Mouse P388 leukemia | $ED_{50} = 26 \times 10^{-6}$ | $ED_{50} > 126 \times 10^{-6}$ |

Compound SRG-8, an analogue of RG-14 that lacks the conjugated carbon-carbon double bond (see below), did not show detectable anticancer cell growth activity, as shown in Table 2, in accord with the expectation that the carbon-carbon double bond in conjugation with the nitro group is an important aspect in the functioning of compounds of the invention herein described.

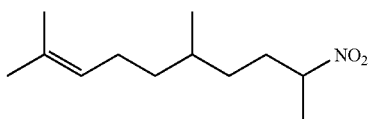

5,9-Dimethyl-2-nitro-8-decene (SRG-8)

An additional embodiment of Formula (I) is one that incorporates an aromatic group for enhanced binding to the hydrophobic binding site of FTase or GGTase, exemplified by the following compound, although there are numerous variations conceivable by those skilled in the art, having regard for this disclosure:

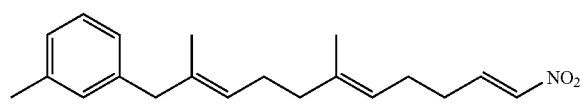

6,10-Dimethyl-11-(3-methylphenyl)-1-nitroundeca-1,5,9-triene

As the isoprenoid farnesyl diphosphate is also a substrate for the enzyme squalene synthase, which is involved in the biosynthesis of cholesterol, the $G_1$, $G_2$, and/or $G_3$ group of compounds of Formula (I) may advantageously be designed to confer specificity of the compound on FTase in cancer cells in preference to squalene synthase based on the known preferences of these two enzymes for particular isoprenoid-type structures, thereby conferring additional specificity of the compound for FTase, with potential reduction in interference with normal background metabolism of cells and less systemic toxicity to patients. For example, anilinogeranyl diphosphate is known to have specificity for FTase over squalene synthase. Thus, the anilinogeranyl group may advantageously be used as a group $G_1$ in a compound of Formula (I) to confer specificity of the compound on FTase over squalene synthase, as shown by the following specific example:

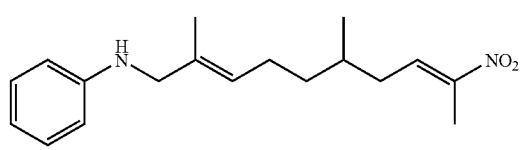

5,9-Dimethyl-2-nitro-10-(phenylamino)-deca-2,8-diene

Compounds of this invention may obtain their specificity for the prenylation enzymes on the basis of chemical features that impart structural similarities to the other natural substrate of prenylation enzymes, namely the protein recipient of the isoprenoid group, as shown hereinabove in equation (1). In this embodiment, the group $G_1$ of Formula (I) is a peptidic group, or a peptidomimetic group, known or expected to bind preferentially to prenylation enzymes and L is used as a suitable linker providing a preferable spatial relationship between $G_1$ and the electrophilic conjugated nitro alkene moiety, defined by one or more carbon-carbon double bonds in conjugation with an attached nitro group ($NO_2$).

The peptidic group or peptidomimetic group $G_2$ in Formula (I) in a preferred embodiment of this invention could be similar to the Cys-a-a-X recognition sequence of the protein substrates of the prenylation enzymes or could be a peptidomimetic group with affinity for prenylation enzymes. An example of such a compound is the following:

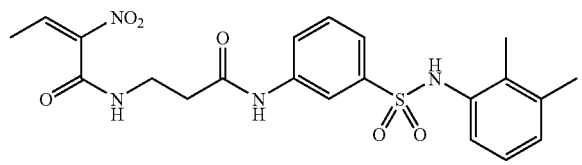

2-Nitro-2-butenoic acid {2-[3-(2,3-dimethylphenylsulfamoyl)-phenylcarbamoyl]-ethyl}-amide In yet another preferred embodiment of this invention with a structure specified by Formula (I), the groups $G_1$ and $G_2$ comprise, respectively, an isoprenoid or other hydrophobic group (for example, but not limited to, a polymethylene chain), and a peptidomimetic group with known or expected affinity for prenylation enzymes, thereby providing a bisubstrate analogue with expected enhanced binding strength and specificity for a prenylation enzyme such as FTase. Specific examples of such embodiments are the following:

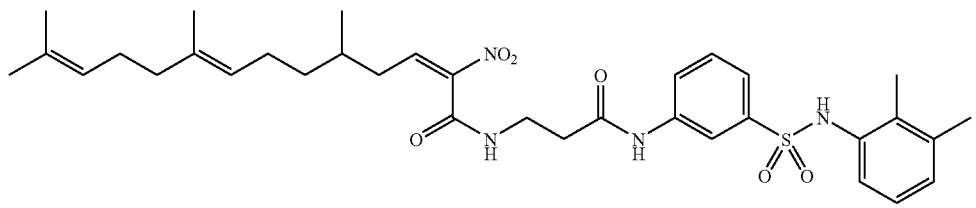

5,9,13-Trimethyl-2-nitrotetradeca-2,18,12-trienoic acid {2-[3-(2,3-dimethylphenylsulfamoyl)-phenylcarbamoyl]-ethyl}-amide

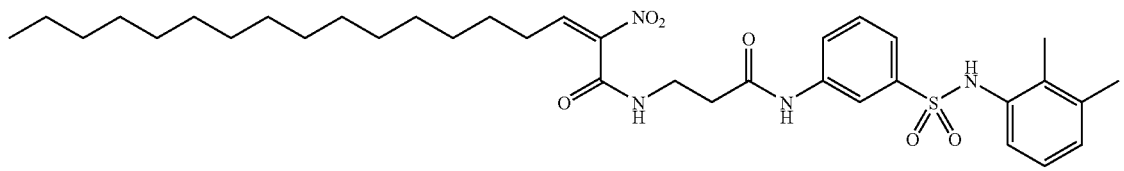

2-Nitro-2-octadecenoic acid {2-[3-(2,3-dimethylphenylsulfamoyl)-phenylcarbamoyl]-ethyl}-amide In yet another preferred embodiment of this invention with a structure specified by Formula (I), the groups $G_1$ and $G_2$, respectively, would comprise an isoprenoid-mimetic group that has specificity for FTase over squalene synthase, and a peptidomimetic group with known or expected affinity for prenylation enzymes, with the potential advantages noted hereinabove:

-continued

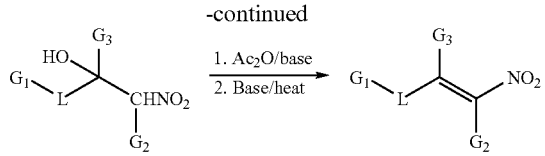

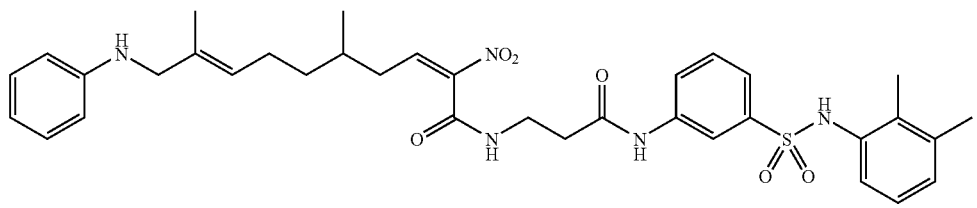

5,9-Dimethyl-2-nitro-10-phenylaminodeca-2,8-dienoic acid {2-[3-(2,3-dimethylphenylsulfamoyl)-phenylcarbamoyl]-ethyl}-amide One of the many ways to synthesize conjugated nitro alkenes is by the Henry reaction followed by elimination, shown in general form by equation (3) below:

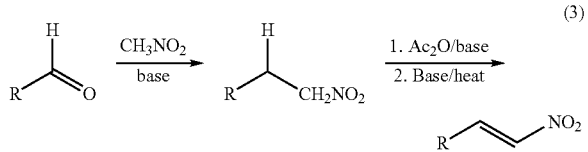
(3)

Illustrated with compounds bearing substituents $G_1$, $G_2$, and $G_3$, the reaction is:

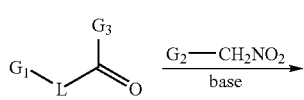
(4)

Combination therapy methods comprising the administration of compounds of this invention and the simultaneous or sequential administration of other anticancer agents to produce synergistic effects of benefit to the patient are also possible. Combination therapy might be based on two strategies. One is to interfere with a different biochemical process from prenylation, e.g., DNA topoisomerase inhibition. This might hamper the development of drug resistance by tumor cells, which is less likely to occur simultaneously in tumor cells exposed to anticancer agents based on interference with different biochemical pathways in the tumor cells.

Another strategy might be to augment the effects of compounds of Formula (I) by co-therapy with a statin drug, which reduces the biosynthesis of endogenous isoprenoid substrates such as farnesyl diphosphate. Such substrates compete with compounds of Formula (I) for the prenylation enzyme active site. The effectiveness of the compounds of Formula (I) could be enhanced by reduction of competition by the natural substrates for the prenylation enzyme active site, with the overall beneficial increase in tumor cell killing.

The term "alkyl," as used alone or in combination herein, refers to an unsubstituted or optionally substituted, straight, or branched-chain saturated hydrocarbon group containing from one to twenty-five carbon atoms, preferably from one to fifteen carbons, such as methyl, ethyl, n-propyl, n-butyl, pentyl, hexyl, heptyl, octyl, the various branched-chain isomers thereof, such as isopropyl, isobutyl, sec-butyl, tert-butyl, isohexyl and the like. The alkyl group may be optionally substituted by one or more substituents, and generally no more than three, and most often just one substituent. Preferred optional substituents include halo, alkoxy, amino, mono- and di-substituted amino, aryl, carboxylic acid, heterocyclo, heteroaryl, cycloalkyl, hydroxyl, trifluoromethoxy and the like.

The term "alkoxy," as used alone or in combination herein, refers to an alkyl group, as defined above, covalently bonded to the parent molecule through an —O— linkage, such as methoxy, ethoxy, propoxy, isopropoxy, butoxy, t-butoxy and the like.

The term "aryloxy," as used alone or in combination herein, refers to an aryl group, as defined below, covalently bonded to the parent molecule through an —O— linkage. An example of an aryloxy is phenoxy.

The term "cycloalkoxy," as used alone or in combination herein, refers to a cycloalkyl group, as defined below, covalently bonded to the parent molecule through an —O— linkage.

The term "alkylthio," as used alone or in combination herein, refers to an alkyl group, as defined above, covalently bonded to the parent molecule through an —S— linkage. The sulfoxide and sulfone derivatives of "alkylthio" are those oxidized derivatives wherein the —S— linkage is oxidized to —SO— and —$SO_2$—, respectively.

The term "alkenyl," as used alone or in combination herein, refers to an alkyl group, as defined above, containing one or more carbon-carbon double bonds. Examples of alkenyl include ethenyl, propenyl, 1,3-butadienyl, and 1,3,5-hexatrienyl. With respect to the substituent $G_1$ in compounds of Formula (I), when $G_1$ is alkenyl, it preferably contains at least two carbon-carbon double bonds. More preferably, $G_1$ is a branched alkenyl, preferably farnesyl (3,7,11-trimethyldodeca-2,6,10-trienyl) or geranylgeranyl (3,7,11,15-tetramethylhexadeca-2,6,10,14-tetraenyl), or partially saturated derivatives thereof. Partially saturated derivatives of farnesyl or geranylgeranyl include radical groups that are identical in structure to native farnesyl or geranylgeranyl but are hydrogenated at one or more of the olefinic (carbon-carbon double bond) sites in the native group to yield a paraffinic (carbon-carbon single bond) site. An example of a partially saturated derivative of farnesyl is shown in the compound designated as RG-4, wherein the substituent $G_1$ that is bonded to the nitro alkene is 2,6,10-trimethylundeca-5,9-dienyl, which is a radical of a diene rather than a triene.

The term "alkynyl," as used alone or in combination herein, refers to an alkyl group, as defined above, containing one or more carbon-carbon triple bonds, preferably one or two such triple bonds.

The term "cycloalkyl," as used alone or in combination herein, refers to an unsubstituted or optionally substituted, saturated cyclic hydrocarbon group containing three to eight carbon atoms. The cycloalkyl group may optionally be substituted by one or more substituents, and generally no more than three, and most often just one substituent. Preferred optional substituents include alkyl, halo, amino, mono- and di-substituted amino, aryl, hydroxyl and the like.

The term "haloallyl," as used alone or in combination herein, is a species of alkyl as defined herein, and particularly refers to an alkyl, substituted with one or more halogen atoms, and preferably is a $C_1$ to $C_4$ alkyl substituted with one to three halogen atoms. One example of a haloalkyl is trifluoromethyl. Preferred examples of haloalkyl groups include trichloromethyl, trifluoromethyl, and perfluoroethyl.

The term "alkanoyl," as used alone or in combination herein, refers to an acyl radical derived from an alkanecarboxylic acid (alkyl-C(O)—) and includes such examples as acetyl, propionyl, butyryl, valeryl, and 4-methylvaleryl.

The term "aroyl," as used alone or in combination herein, means an acyl radical derived from an aromatic carboxylic acid, such as optionally substituted benzoic or naphthoic acids and specifically including benzoyl and 1-naphthoyl.

The term "aminocarbonyl," as used alone or in combination herein means an amino-substituted carbonyl (carbamoyl or carboxamide) wherein the amino group is a primary amino (—$NH_2$). Substituted aminocarbonyl refers to secondary (mono-substituted amino) or tertiary amino (di-substituted amino) group, as defined below.

The term "aminoalkanoyl," as used alone or in combination herein, means an amino-substituted alkanoyl wherein the amino group is a primary amino group (-alkyl-C(O)—$NH_2$). The term "substituted aminoalkanoyl" refers to related secondary (mono-substituted amino) or tertiary amino (di-substituted amino) group, as defined below.

The term "carbocycloalkyl," as used alone or in combination herein, refers to an unsubstituted or optionally substituted, stable, saturated or partially unsaturated monocyclic, bridged monocyclic, bicyclic, or spiro ring carbocycle of 3 to 15 carbon atoms such as cyclopropyl, cyclobutyl, cyclopentyl, cyclohexyl, cycloheptyl, bicyclohexyl, bicyclooctyl, bicyclononyl, spirononyl and spirodecyl. Cycloalkyls are thus one specific subset of carbocycloalkyls. The term "optionally substituted" as it refers to "carbocycloalkyl" herein indicates that the carbocycloalkyl group may be substituted at one or more substitutable ring positions by one or more groups independently selected from alkyl, alkoxy, nitro, monoalkylamino, dialkylamino, cyano, halo, haloalkyl (preferably trifluoromethyl), alkanoyl, aminocarbonyl, monoalkylaminocarbonyl, dialkylaminocarbonyl, alkylamido, alkoxyalkyl, alkoxycarbonyl, alkylcarbonyloxy and aryl (preferably phenyl), said aryl being optionally substituted by halo, alkyl and/or alkoxy groups.

The term "heterocyclo," as used alone or in combination herein, refers to an unsubstituted or optionally substituted, stable, saturated, or partially unsaturated, monocyclic, bridged monocyclic, bicyclic, or spiro ring system containing carbon atoms and other atoms selected from nitrogen, sulfur and/or oxygen. Preferably, a heterocyclo group is a 5 or 6-membered monocyclic ring or an 8-11 membered bicyclic ring that consists of carbon atoms and contains one, two, or three heteroatoms selected from nitrogen, oxygen and/or sulfur. Heterocyclo includes bent-fused monocyclic cycloalkyl groups having at least one such heteroatom. The term "optionally substituted," as it refers to "heterocyclo" herein, indicates that the heterocyclo group may be substituted at one or more substitutable ring positions by one or more groups independently selected from alkyl (including haloalkyl (preferably trifluoromethyl)), alkoxy, nitro, monoalkylamino, dialkylamino, cyano, halo, alkanoyl, aminocarbonyl, monoalkylaminocarbonyl, dialkylaminocarbonyl, alkylamido, alkoxyalkyl, alkoxycarbonyl, alkylcarbonyloxy and aryl (preferably phenyl), said aryl being optionally substituted by halo, alkyl and alkoxy groups. The heterocyclo group may be, and generally is, attached to the parent structure through a carbon atom, or alternatively may be attached through any heteroatom of the heterocyclo group that results in a stable structure.

The term "heteroaryl," as used alone or in combination herein, refers to an unsubstituted or optionally substituted, stable, aromatic monocyclic or bicyclic ring system containing carbon atoms and other atoms selected from nitrogen, sulfur and/or oxygen. Preferably, a heteroaryl group is a 5- or 6-membered monocyclic ring (optionally benzo-fused) or an 8- to 11-membered bicyclic ring that consists of carbon atoms and contains one, two, or three heteroatoms selected from nitrogen, oxygen and/or sulfur. The term "optionally substituted" as it refers to "heteroaryl" herein indicates that the heteroaryl group may be substituted at one or more substitutable ring positions by one or more groups independently selected from alkyl (including haloalkyl (preferably trifluoromethyl)), alkoxy, nitro, monoalkylamino, dialkylamino, cyano, halo, alkanoyl, aminocarbonyl, monoalkylaminocarbonyl, dialkylaminocarbonyl, alkylamido, alkoxyalkyl, alkoxycarbonyl, alkylcarbonyloxy, and aryl (preferably phenyl), said aryl being optionally substituted by halo, alkyl, and alkoxy groups. The heteroaryl group may be, and generally is attached to the parent structure through a carbon atom or alternatively may be attached through any heteroatom of the heteroaryl group that results in a stable structure. In the foregoing structures it is also contemplated that a nitrogen could be replaced with an N-oxide. Both heterocyclo and heteroaryl also are intended to embrace benzo-fused structures such as 1,2-methylenedioxybenzene and 1,4-benzodioxan. Preferred examples of heteroaryl groups include pyridyl (e.g., 2-, 3-, or 4-pyridyl).

The terms "halo" and "halogen," as used alone or in combination herein, represent fluorine, chlorine, bromine or iodine, preferably fluorine or chlorine for enzyme affinity, and preferably chlorine, bromine, or iodine when a nucleofuge.

The term "aryl," as used alone or in combination herein, refers to an unsubstituted or optionally substituted monocyclic or bicyclic aromatic hydrocarbon ring system having 6 to 12 ring carbon atoms. Preferred are optionally substituted phenyl, 1-naphthyl, or 2-naphthyl groups. The aryl group may optionally be substituted at one or more substitutable ring positions (generally at no more than three positions and most often at one or two positions) by one or more groups independently selected from alkyl (including haloalkyl (preferably trifluoromethyl and difluoromethyl)), alkenyl, alkynyl, alkoxy, aryloxy, nitro, hydroxyl, amino, mono- and di-substituted amino, cyano, halo, alkanoyl, aminocarbonyl, carboxylic acid, carboxylic acid esters, carboxylic acid amide, an optionally substituted phenyl (optionally substituted by halo, alkyl and alkoxy groups), heterocyclo, or heteroaryl. Preferably, the aryl group is phenyl, optionally substituted with up to four and more usually with one or two groups, preferably selected from alkyl, alkoxy, as well as cyano, trifluoromethyl, and halo.

The terms "aralkyl" and "(aryl)alkyl," as used alone or in combination herein, are species of alkyl as defined herein, and particularly refer to an alkyl group as defined above in which one hydrogen atom is replaced by an aryl group as defined above, and include benzyl, and 2-phenylethyl.

The terms "(heterocyclo)alkyl" and "(heteroaryl)alkyl," as used alone or in combination can be considered a species of alkyl as defined herein, and particularly refer to an to an alkyl group as defined above in which one hydrogen atom is replaced by a heterocyclo group as defined above, or by a heteroaryl group as defined above.

The terms "alkoxycarbonyl," as used alone or in combination herein, mean a radical of the formula —C(O)-alkoxy, in which alkoxy is as defined above.

The term "alkylcarbonyloxy," as used alone or in combination herein, means a radical of the formula —O—C(O)-alkyl, in which alkyl is as defined above.

The term "alkoxyalkanoyl," as used alone or in combination herein, means a radical of the formula -alkyl-C(O)—O-alkyl.

The term "carboxyalkyl," as used alone or in combination herein, means a radical of the formula -alkyl-C(O)—OH.

The term "substituted amino," as used alone or in combination herein, embraces both mono and di-substituted amino. These terms, alone, or in combination, mean a radical of the formula —NR'R", where, in the case of mono-substitution, one of R' and R" is a hydrogen and the other is selected from alkyl, cycloalkyl, aryl, heterocyclo, (aryl)alkyl, (heterocyclo)alkyl, heteroaryl and hetero(aryl)alkyl; in the case of di-substitution, R' and R" are independently selected from alkyl, cycloalkyl, aryl, heterocyclo, and heteroaryl, or R' and R" together with the nitrogen atom to which they are both attached form a 3- to 8-membered heterocyclo or heteroaryl radical.

The term "amido," as used alone or in combination herein, refers to the group (—NH—) and the term "substituted amido" embraces a radical of the formula (—NR'—) where R' has the meaning above in connection with substituted amino.

The terms "alkanoylamido," "aroylamido," "heterocyclocarbonylamido" and "heteroaroylamido," as used alone or in combination herein, mean groups of the formula R—C(O)—NH— where R is an alkyl, aryl, heteroaryl or heterocyclo group. The terms "heteroaroyl" and "heterocyclocarbonyl," when used alone or in combination, mean groups of the formula R—C(O)— where R is a heteroaryl or heterocyclo group.

Unless otherwise defined, the term "optionally substituted" as used herein, refers to the substitution of a ring system at one or more positions with one or more groups selected from: $C_1$-$C_5$ alkyl, $C_1$-$C_5$ alkoxy, an optionally substituted phenyl, cyano, halo, trifluoromethyl, $C_1$-$C_5$ alkoxycarbonyl, $C_1$-$C_5$ alkyl carbonyloxy, mono- and bis-($C_1$-$C_5$ alkyl)-carboxamide, $C_1$-$C_5$ alkylamido, nitro, and mono- and bis-($C_1$-$C_5$ alkyl)-amino.

The term "hydrophobic group" as used herein, refers to any of the groups hydrogen, alkyl, alkoxy, alkoxyalkyl, aryloxy, cycloalkoxy, alkylthio, alkenyl, alkynyl, cycloalkyl, haloalkyl, alkanoyl, aroyl, substituted aminocarbonyl, aminoalkanoyl or optionally substituted aminoalkanoyl, carbocycloalkyl or optionally substituted carbocycloalkyl, heterocyclo or optionally substituted heterocyclo, heteroaryl or optionally substituted heteroaryl, halo, aryl, aralkyl, (heterocyclo)alkyl, (heteroaryl)alkyl, alkoxycarbonyl, alkylcarbonyloxy, alkoxyalkanoyl, and alkanoylamido as defined above having at least some hydrophobicity and generally having the properties of poor miscibility with water and low polarity.

It is recognized that there may be some overlap in some of the definitions of the various groups. Specific groups are mentioned, however, in order to emphasize their positive inclusion in the described subject matter, as not only an optional substituent. As used herein, when a particular group, generally understood to have a single point of attachment to a core structure, such as an alkyl group, is identified in connection with a structure that must have two points of attachment in the structural core, it is understood that the named group (e.g., alkyl) refers to the parent group with a hydrogen atom or a site of unsaturation removed to create the second point of attachment so as to provide the required structure.

The terms "substrate-mimicking isoprenoid" or "isoprenoid mimetic" refer to chemical structures that structurally and/or functionally mimic the activity of isoprenoids in terms of their recognition by, and affinity for, prenylation enzymes such as farnesyltransferase and geranylgeranyltransferase I and II. Isoprenoid mimetics are known in the art and are described, for example, by M. Schlitzer et al., *Bioorganic and Medicinal Chemistry*, 8(8):1991-2006 (2000) and by M. Schlitzer et al., *Bioorganic and Medicinal Chemistry*, 8(10):2399-2406 (2000).

The term "peptidomimetic" or the phrase "mimetic of a peptide" refers to chemical structures that contain nonpeptidic structural elements and that structurally and/or functionally mimic the biological or biochemical activity of certain peptides, and in particular mimic specific peptide recognition sequences of enzymes, such as prenylation enzymes, that are targeted for inhibition. While peptidomimetics retain enzyme inhibition function, they are less susceptible than their corresponding native proteins to natural enzymatic degradation (e.g., cleavage) under physiological conditions. Peptidomimetics of cell division proteins, which act as substrates for prenylation enzymes such as farnesyltransferase and geranylgeranyltransferase I and II are known in the art and are described, for example, by H. Waldmann and M. Thutewohl, *Topics in Chemistry*, 211: 117-130 (2000); M. Schlitzer, et al., *Archiv der Pharmazie, Pharmaceutical and Medicinal Chemistry*, 332(4):124-132 (1999); M. A. Kothare, et al., *Tetrahedron*, 56:9833-9841 (2000); N.-H. Nam and K. Parang, *Current Drug Targets*, 4(2):159-179 (2003); and F. A. L. M. Eskens, et al., *Cancer Treatment Reviews*, 26:319-332 (2000).

The term "effective amount" means the dose or effective amount to be administered to a patient and the frequency of administration to the subject which is sufficient to obtain a therapeutic effect (e.g., inhibition of tumor growth or reversion of tumor cells to a normal phenotype, inhibition of the proliferation of cancer cells, inhibition of a CDP prenylation enzyme, or inhibition of CDP prenylation) as readily determined by one or ordinary skill in the art, by the use of known techniques and by observing results obtained under analogous circumstances. In determining the therapeutically effective amount or dose, a number of factors are considered by the attending diagnostician, including but not limited to, the potency and duration of action of the compounds used; the nature and severity of the illness to be treated as well as on the sex, age, height, weight, body surface area, general health and individual responsiveness of the patient to be treated, and other relevant circumstances.

The phrase "therapeutically effective" indicates the capability of an agent to prevent, or improve the severity of, the disorder or its undesirable symptoms, while avoiding adverse side effects typically associated with alternative therapies.

Those skilled in the art will appreciate that dosages may also be determined with guidance, for example, from Goodman & Goldman's The Pharmacological Basis of Therapeutics, Ninth Edition (1996), Appendix II, pp. 1707-1711 or from Goodman & Goldman's The Pharmacological Basis of Therapeutics, Tenth Edition (2001), Appendix II, pp. 475-493. With respect to conventional prenylation enzyme inhibitors, guidance may be obtained from art-recognized dosage amounts as described, for example, by J. E. Karp, et al., *Blood*, 97(11):3361-3369 (2001) and A. A. Adjei, et al., *Cancer Research*, 60:1871-1877 (2000).

The term "pharmaceutically acceptable" is used herein to mean that the modified noun is appropriate for use in a pharmaceutical product. Pharmaceutically acceptable cations include metallic ions and organic ions. More preferred metallic ions include, but are not limited to, appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

Also included in connection with use of the method(s) of the present invention are the isomeric forms and tautomers and the pharmaceutically acceptable salts of the present invention. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric and galacturonic acids.

Suitable pharmaceutically acceptable base addition salts of compounds used in connection with the method(s) of the present invention include metallic ion salts and organic ion salts. More preferred metallic ion salts include, but are not limited to, appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

The term "ester" refers to a derivative of a parent compound that has similar or identical pharmacological activity and is modified to have the chemical linkage R—C(O)OR'. Thus, for example, a methyl ester derivative is obtained when R'=CH$_3$. The preparation of esters is well documented in standard chemistry textbooks. See, e.g., Morrison and Boyd, Organic Chemistry, 5$^{th}$ Ed., Allyn and Bacon, Inc., pp. 668, 830, 841-843 and 872-874 (1987), which describes conversion of alcohols into esters by acylation of the hydroxyl group (i.e., R'OH→R—C(O)OR'), or equivalently, conversion of acids into esters by replacement of the OH group of —C(O)OH by OR' (i.e., R—C(O)OH→R—(O)OR').

The term "prodrug" refers to a form of the compound that has been chemically modified and becomes pharmaceutically active under physiological conditions (i.e., in the body). A prodrug may be biologically inactive at its site of action, but in this case it is degraded or modified, either (1) under physiological conditions or (2) by one or more enzymatic or other in vivo processes to the parent, bioactive form. Generally, a prodrug has a different pharmacokinetic profile than the parent compound such that, for example, it is more easily absorbed across the mucosal epithelium, it has better salt formation or solubility, and/or it has better systemic stability (e.g., an increased half-life).

Those skilled in the art recognize prodrugs as chemically-modified pharmaceutical compounds that include (1) terminal ester or amide derivatives that are susceptible to being cleaved by esterases or lipases, (2) terminal peptide derivatives that may be recognized by specific or nonspecific proteases, (3) derivatives that cause accumulation at a site of action through membrane selection, and (4) forms having various combinations of these modifications.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more anticancer agents or agents administered to reduce the side effects associated with a particular treatment regimen. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes that are obvious to one skilled in the art are intended to be within the scope and nature of the invention.

From the foregoing description, one skilled in the art can easily ascertain the essential characteristics of this invention, and without departing from the spirit and scope thereof, can make various changes and modifications of the invention to adapt it to various usages and conditions.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

In summary an improved method of interference with protein prenylation has been described that may prevent or hamper the proliferation of tumor cells, possibly resulting in a decrease in tumor size and/or disappearance of the cancer, to the benefit of cancer patients.

EXAMPLE 1

The abbreviations used in this example are: Ac$_2$O, acetic anhydride; Ds-GCVLS, the dansyl-labeled pentapeptide N-dimethylaminonaphthalenesulfonyl-Gly-Cys-Val-Leu-Ser; DTT, dithiothreitol; Fmoc, 9-fluorenylmethoxycarbonyl; FTase, human recombinant protein farnesyltransferase; HEPES, N-2-hydroxyethylpiperazine-N'-2-ethanesulfonic acid; PCC, pyridinium chlorochromate; THF, tetrahydrofuran; Tris, tris(hydroxymethyl)aminomethane. $^1$H NMR spectra were measured at 300 MHz in CDCl$_3$ and chemical shifts ($\delta$) are reported in ppm relative to internal (CH$_3$)$_4$Si or to residual CHCl$_3$ at $\delta$ 7.26.

Preparation of 5,9,13-trimethyl-2-nitrotetradeca-2,8,12-triene (RG-4)—This substance was prepared as summarized in Scheme 1 and as described in detail following the caption:

Scheme 1.

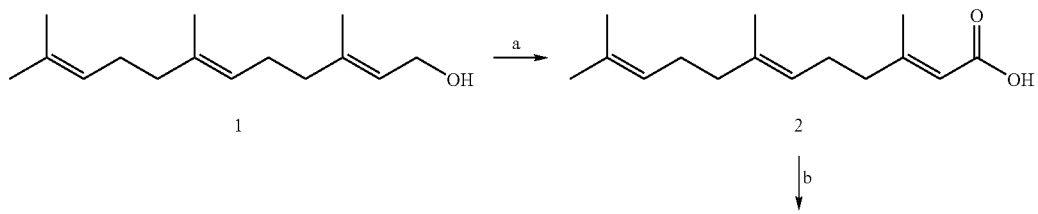

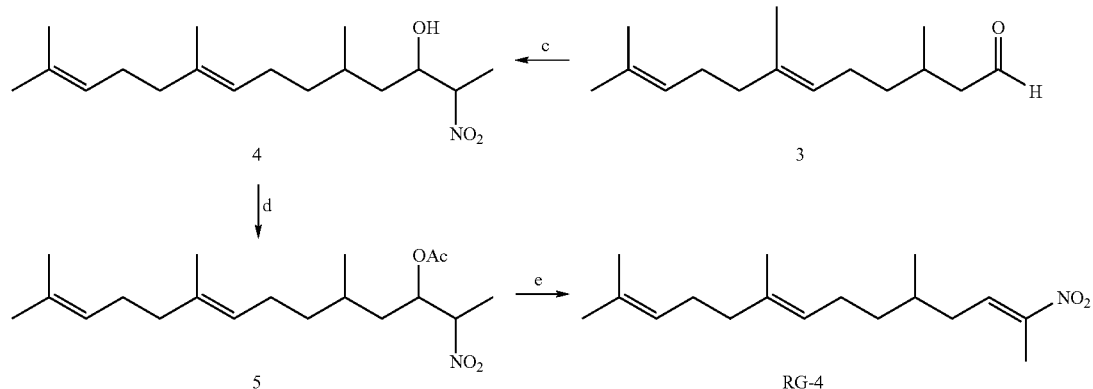

a. PCC/CH$_2$Cl$_2$, room temp., 24 h.
b. NiCl$_2$·6H$_2$O/Al/THF, room temp., 6 h.
c. Nitroethane/Amberlyst A-21, room temp., 24 h.
d. AC$_2$O/cat. H$_2$SO$_4$ -10° C., 15 min.
e. t-BuOK/t-BuOH, room temp., 1 h.

Farnesal (2). To a stirred solution of 15 g of PCC in 250 mL of dichloromethane was added 10 g of (E,E)-farnesol (1). The reaction mixture was stirred at room temperature overnight and filtered through a 55-cm (height) by 5-cm (diameter) column of silica gel. The eluate was dried over MgSO$_4$, and the solvent was removed by rotary evaporation to give a greenish-yellow oil. The crude farnesal was purified by column chromatography (silica gel/chloroform) to yield 7.25 g of product 2, predominantly the (E,E)-isomer. $^1$H NMR δ (ppm) 10.0 (d, CHO), 5.9 (d, CH$_2$C(CH$_3$)=CHCO), 5.1 (t, CH$_3$C(CH$_3$)=CH and CH$_2$C(CH$_3$)=CH), 2.3 (m, CH$_2$C(CH$_3$)=CH—CO), 2.5 (m, CH$_2$C(CH$_3$)=CHCH$_2$CH$_2$), 2.2 (s, CH$_3$C=CH—CO), 2.0 (m, CH$_3$C(CH$_3$)=CHCH$_2$CH$_2$), 1.6-1.7 (all s, CH$_3$C(CH$_3$)=CHCH$_2$CH$_2$CCH$_3$).

Dihydrofarnesal (3). To a stirred solution of 0.53 g of 2 in 150 mL of dry THF in a round-bottom flask equipped with a water-cooled condenser was added a solid mixture of 31.04 g of NiCl$_2$.6H$_2$O and 4.27 g of Al powder (caution: exothermic). The reaction mixture was stirred at room temperature for 6 h. The solid mass was removed by filtration, and the solvent was dried over MgSO$_4$ and removed by rotary evaporation, which afforded 0.50 g of racemic 3, predominantly the (E)-isomer. $^1$H NMR δ (ppm) 9.8 (t, CHO), 5.2 (t, CH$_3$C(CH$_3$)=CH and CH$_2$C(CH$_3$)=CH), 2.3 (m, CH$_2$C(CH$_3$)=CH), 2.2-2.4 (qd, CH$_2$CHO), 2.0 (m, C=CHCH$_2$CH$_2$C(CH$_3$)=CHCH$_2$), 1.6-1.7 (all s, CH$_3$C(CH$_3$)=CHCH$_2$CH$_2$CCH$_3$), 1.2-1.5 (m, CH$_2$CH(CH$_3$)CH$_2$CO), 0.9 (d, CH$_2$C(CH$_3$)=CH).

5,9,13-Trimethyl-2-nitrotetradeca-8,12-dien-3-ol (4). To 2.93 g of 3 was added 5 mL of nitroethane with stirring. Approximately 5-6 g of Amberlyst A-21 was added, and the mixture was stirred at room temperature overnight. The mixture was filtered and the ion exchange resin was rinsed four times with 25 mL of dichloromethane. The filtrate was dried over anhydrous MgSO$_4$, and the solvent was removed by rotary evaporation, which afforded 3.53 g (90%) of a mixture of stereoisomers of the desired nitro alcohol 4. $^1$H NMR δ (ppm) 5.2 (t, CH$_3$C(CH$_3$)=CH and CH$_2$C(CH$_3$)=CH), 4.4 (m, CHNO$_2$), 2.2 (br s, CHOH), 2.0 (m, C=CHCH$_2$CH$_2$C(CH$_3$)=CHCH$_2$), 1.6-1.7 (all s, CH$_3$C(CH$_3$)=CHCH$_2$CH$_2$CCH$_3$), 1.5 (d, CH$_3$CHNO$_2$), 1.2-1.5 (m, CH$_2$CH(CH$_3$)CH$_2$), 0.9 (d, CH$_2$CH(CH$_3$)CH$_2$).

5,9,13-Trimethyl-2-nitrotetradeca-8,12-dien-3-yl acetate (5). A flask containing 1.15 g of acetic anhydride was cooled to -10° C. with a salt-ice bath, and 3.1 g of 4 was added with magnetic stirring under an N$_2$ atmosphere. After 10-15 min, 25 mL of concentrated H$_2$SO$_4$ was added. The reaction mixture was allowed to stir for an additional 10 min, after which it was diluted with 40 mL of ether and 10 mL of H$_2$O. The mixture was extracted three times with 15 mL of saturated aqueous sodium bicarbonate and once with 10 mL of saturated aqueous NaCl. The ether layer was dried over anhydrous MgSO$_4$, and the solvent was removed by rotary evaporation to yield 1.40 g of a mixture of stereoisomers of the nitro acetate 5. $^1$H NMR δ (ppm) 5.4 (br m, CHOCOCH$_3$), 5.2 (t, CH$_3$C(CH$_3$)=CH and CH$_2$C(CH$_3$)=CH), 4.4 (m, CHNO$_2$), 2.1 (s, CH$_3$CO$_2$), 2.0 (m, C=CHCH$_2$CH$_2$C(CH$_3$)=CHCH$_2$), 1.6-1.7 (all s, CH$_3$C(CH$_3$)=CHCH$_2$CH$_2$CCH$_3$), 1.5 (d, CH$_3$CHNO$_2$), 1.2-1.5 (m, CH$_2$CH(CH$_3$)CH$_2$), 0.9 (d, CH$_2$CH(CH$_3$)CH$_2$).

5,9,13-Trimethyl-2-nitrotetradeca-2,8,12-triene (RG-4). A solution of 1.30 g of 5 in 25 mL of t-butyl alcohol was added to a solution of 30 mL of t-butyl alcohol containing 0.53 g of potassium t-butoxide. The reaction mixture was stirred at room temperature for 1 h, whereupon it was added to 150 mL of ether and 20 mL of H$_2$O. The organic layer was separated and dried over MgSO$_4$, and the solvent was removed by rotary evaporation to afford 0.40 g of racemic RG-4, predominantly the (E)-isomer. $^1$H NMR δ (ppm) 7.18 (t, CH=CNO$_2$), 5.2 (t, CH$_3$C(CH$_3$)=CH and CH$_2$C(CH$_3$)=CH), 2.19 (s, C=C(CH$_3$)NO$_2$), 2.0 (m, C=CHCH$_2$CH$_2$C(CH$_3$)=CHCH$_2$), 2.2-2.3 (m, CH$_2$C=CNO$_2$), (CH$_3$C=(CH$_3$), 1.6-1.7 (all s, CH$_3$C(CH$_3$)=CHCH$_2$CH$_2$CCH$_3$), 1.2-1.5 (m, CH$_2$CH(CH$_3$)CH$_2$), 0.95 (d, CH$_2$CH(CH$_3$)CH$_2$).

Preparation of Ds-GCVLS—Ds-GCVLS was prepared by a method analogous to a published procedure. Synthesis was performed by use of a Millipore 9050 Plus PepSynthesizer that employed standard Fmoc solid phase peptide synthesis methodology. PS-PEG resin and Fmoc protected amino acids were obtained from Millipore. The N-dansylglycine was from Sigma Chemical Co. Peptide purification was performed by RP-HPLC on an Alltech Macrosphere RP300 C8 column. Elution was accomplished with a linear gradient from aqueous 10 mM trifluoroacetic acid to 10 mM trifluoroacetic acid in acetonitrile. Lyophilization yielded a pale yellow solid. Stock solutions were prepared in 50 mM Tris containing 5 mM DTT and 0.2% n-octyl-β-D-glucopyranoside (Anatrace, Inc.), pH 7.7. Concentrations of Ds-GCVLS were determined by use of the extinction coefficient of the dansyl group at 340 nm ($\epsilon$=4250 M-1 cm-1). Stock solutions were stored at −20° C. FTase (stored at −70° C.) was a generous gift from Professor Patrick Casey at Duke University.

FTase assay—The fluoresence assay conditions were adapted from a published method. The FTase assay consisted of the measurement of the rate of FTase-catalyzed farnesylation of the fluorescent pentapeptide Ds-GCVLS. Upon farnesylation of the cysteine, the fluoresence emission at $\lambda$=505 nm of the dansyl group is enhanced due to the proximity of the hydrophobic isoprenoid group. Enzyme activity (approximately 60 nM FTase) was monitored at saturating substrate concentrations (10 µM farnesyl diphosphate, ammonium salt, prepared by successive dilutions of a commercial 2.3 mM solution in methanol:10 mM aqueous NH4OH (7:3) into assay buffer, and 1.0 µM Ds-GCVLS) by measurement of the increase in fluorescence emission observed at $\lambda$=505 nm as FTase farnesylated Ds-GCVLS for a period of 10 min. The assay buffer consisted of 50 mM NaHEPES, 5 mM DTT, 5 mM $MgCl_2$, 10 µM $ZnCl_2$, and 0.2% n-octyl-β-D-glucopyranoside, pH 7.5. Fluorescence emission was measured with a JASCO FP-77 spectrofluorimeter fitted with a temperature-controlled cuvette holder connected to a 30° C. constant temperature bath. All fluorescence assays were conducted in a 4 mm×4 mm quartz cuvette with excitation at 340 nm.

Inhibition of FTase by 5,9,13-trimethyl-2-nitrotetradeca-2,8,12-triene (RG-4)—FTase was incubated at 30° C. in the presence and absence of 5,9,13-trimethyl-2-nitrotetradeca-2,8,12-triene (RG-4) at various concentrations in 50 mM NaHEPES, 5 mM $MgCl_2$, 10 µM $ZnCl_2$, and 0.2% n-octyl-β-D-glucopyranoside, pH 7.5 (i.e., assay buffer without DTT). After 30 minutes, aliquots of the reaction mixture were removed and assayed for FTase activity. A control was handled as above, except that 5,9,13-trimethyl-2-nitrotetradeca-2,8,12-triene (RG-4) was omitted from the incubation mixture. In this way 5,9,13-trimethyl-2-nitrotetradeca-2,8,12-triene (RG-4) at a concentration of 50 µM was found to inhibit FTase to the extent of 83% after a 30-min treatment in vitro. At a concentration of 5 µM, it decreased FTase activity by 35%.

Cancer cell growth inhibition. Treatment of human cancer cells grown in culture with 5,9,13-trimethyl-2-nitrotetradeca-2,8,12-triene (RG-4) at various concentrations resulted in cancer cell growth inhibition, as reported in Table 1.

EXAMPLE 2

Synthesis of 5,9-dimethyl-2-nitrodeca-2,8-diene (RG-14) was by a method analogous to that of 5,9,13-trimethyl-2-nitrotetradeca-2,8,12-triene (RG-4), described in Example 1, as follows:

5,9-Dimethyl-2-nitrodec-8-en-3-ol (6). Nitroethane (7.5 g) was added to a stirred solution of 13.82 g of citronellal in dichloromethane. Approximately 12-14 g of Amberlyst A-21 ion exchange resin was added, and the mixture was stirred at room temperature overnight. After filtration, the resin was rinsed 4 times with 75 mL of dichloromethane. The filtrate was dried over anhydrous $MgSO_4$ and the solvent was removed by rotary evaporation, affording 20.1 g (95%) of a mixture of stereoisomers of the desired nitro alcohol 6. $^1$H NMR δ (ppm) 5.2 (t, C=CH), 4.4 (m, $CH_3CHNO_2$), 2.5 (broad s, CHOH), 2.0 (br m, =CHCH$_2$), 1.60 and 1.65 (both s, $CH_3C(CH_3)$=), 1.5 (d, $CH_3CHNO_2$), 1.2-1.5 (m, $CH_2CH(CH_3)CH_2$), 0.95 (d, $CH_2CH(CH_3)CH_2$).

5,9-Dimethyl-2-nitrodec-8-en-3-yl acetate (7). A flask containing 1.3 g of acetic anhydride was cooled to −10° C. with a salt-ice bath, and 2.34 g of 6 was added with magnetic stirring under an $N_2$ atmosphere. After 10-15 min, 2-5 drops of concentrated $H_2SO_4$ were added. The reaction mixture was allowed to stir for an additional 10 min, after which it was treated with 40 mL of ether and 10 mL of $H_2O$. The mixture was extracted three times with 15 mL of saturated aqueous sodium bicarbonate and once with 10 mL of saturated aqueous NaCl. The ether layer was dried over anhydrous $MgSO_4$, and the solvent was removed by rotary evaporation to yield 2.41 g (88%) of a mixture of stereoisomers of the nitro acetate 7. $^1$H NMR δ (ppm) 5.4 (broad m, $CH_2CH(OAc)$), 5.2 (t, C=CH), 4.65 (m, $CH_3CHNO_2$), 2.1 (s, $CH_3CO_2$), 2.0 (br m, =CHCH$_2$), 1.60 and 1.65 (both s, $CH_3C(CH_3)$=), 1.5 (d, $CH_3CHNO_2$), 1.2-1.5 (m, $CH_2CH(CH_3)CH_2$), 0.95 (d, $CH_2CH(CH_3)CH_2$).

5,9-Dimethyl-2-nitrodeca-2,8-diene (RG-14). A solution of 0.84 g of 7 in 10 mL of t-butyl alcohol was added to a solution of 5 mL of t-butyl alcohol containing 0.38 g of potassium t-butoxide. The reaction mixture was stirred at room temperature for 1 h, whereupon it was added to 150 mL of ether and 20 mL of $H_2O$. The organic layer was separated and dried over anhydrous $MgSO_4$, and the solvent was removed by rotary evaporation to afford 0.60 g (94%) of racemic (E)- and (Z)-RG-7. $^1$H NMR δ (ppm) 7.18 (t, CH=CNO$_2$), 5.2 (t, $(CH_3)_2$C=CH), 2.2-2.3 (m, $CH_2$C=CNO$_2$), 2.19 (s, $CH_3CNO_2$), 2.0 (br m, $(CH_3)_2$C=CHCH$_2$), 1.60 and 1.65 (both s, $CH_3C(CH_3)$=), 1.2-1.5 (m, $CH_2CH(CH_3)CH_2$), 0.95 (d, $CH_2CH(CH_3)CH_2$).

Cancer cell growth inhibition. Treatment of human cancer cells and mouse cancer cells grown in culture with 5,9-dimethyl-2-nitrodeca-2,8-diene (RG-14) at various concentrations resulted in cancer cell growth inhibition, as reported in Table 2.

EXAMPLE 3

Synthesis of 4,8-dimethyl-1-nitronona-1,7-diene (RG-7) was by a method analogous to that of 5,9,13-trimethyl-2-nitrotetradeca-2,8,12-triene (RG-4), described in Example 1.

Cancer cell growth inhibition. Treatment of human cancer cells grown in culture with 4,8-dimethyl-1-nitronona-1,7-diene (RG-7) at various concentrations resulted in cancer cell growth inhibition, as reported in Table 1.

EXAMPLES 4-53

By use of the synthesis schemes described herein, the following compounds of Formula (Ib') could be prepared, as indicated in Table 3:

TABLE 3

$$\text{(Ib')}$$

| Example | A | G$_2$ | n |
|---|---|---|---|
| 4 (B=H) | prenyl-CH$_2$- | H | 0 |
| 5 (B=CH$_3$) | prenyl-CH$_2$- | | |
| 6 (B=H) | prenyl-CH$_2$- | H | 1 |
| 7 (B=H) | prenyl-CH$_2$- | H | 2 |
| 8 (B=H) | prenyl-CH$_2$- | CH$_3$ | 0 |
| 9 (B=CH$_3$) | prenyl-CH$_2$- | | |
| 10 (B=H) | prenyl-CH$_2$- | CH$_3$ | 1 |
| 11 (B=H) | prenyl-CH$_2$- | CH$_3$ | 2 |
| 12 (B=H) | geranyl-CH- | H | 0 |
| 13 (B=CH$_3$) | geranyl-CH- | | |
| 14 (B=H) | geranyl-CH- | H | 1 |
| 15 (B=CH$_3$) | geranyl-CH- | | |
| 16 (B=H) | geranyl-CH- | H | 2 |

TABLE 3-continued $$\underset{A}{\overset{B}{\diagdown}}\!\!\!\!\diagup\!\!\!\!(\ )_n\!\!\!\!\diagup\!\!\!\!\overset{NO_2}{\underset{G_2}{\diagdown}} \quad (Ib')$$

| Example | A | $G_2$ | n |
|---|---|---|---|
| 17 (B=H) | (3-methylbut-2-enyl) | $CH_3$ | 0 |
| 18 (B=CH$_3$) | (3-methylbut-2-enyl) | $CH_3$ | 0 |
| 19 (B=H) | (3-methylbut-2-enyl) | $CH_3$ | 1 |
| 20 (B=H) | (3-methylbut-2-enyl) | $CH_3$ | 2 |
| 21 (B=H) | (4,8-dimethylnona-3,7-dienyl) | H | 0 |
| 22 (B=CH$_3$) | (4,8-dimethylnona-3,7-dienyl) | H | 0 |
| 23 (B=H) | (4,8-dimethylnona-3,7-dienyl) | H | 1 |
| 24 (B=CH$_3$) | (4,8-dimethylnona-3,7-dienyl) | H | 1 |
| 25 (B=H) | (4,8-dimethylnona-3,7-dienyl) | $CH_3$ | 0 |
| 26 (B=CH$_3$) | (4,8-dimethylnona-3,7-dienyl) | $CH_3$ | 0 |
| 27 (B=H) | (4,8-dimethylnona-3,7-dienyl) | $CH_3$ | 0 |
| 28 (B=CH$_3$) | (4,8-dimethylnona-3,7-dienyl) | $CH_3$ | 1 |
| 29 (B=H) | (4,8-dimethylnona-3,7-dienyl) | $CH_3$ | 1 |
| 30 (B=CH$_3$) | (m-tolylmethyl-substituted alkenyl) | H | 1 |

TABLE 3-continued (Ib')

| Example | A | G$_2$ | n |
|---|---|---|---|
| 31 (B=CH$_3$) | 3-methylbenzyl-CH=C(CH$_3$)-CH$_2$- | CH$_3$ | 1 |
| 32 (B=CH$_3$) | PhNH-CH$_2$-C(CH$_3$)=CH-CH$_2$- | H | 1 |
| 33 (B=CH$_3$) | PhNH-CH$_2$-C(CH$_3$)=CH-CH$_2$- | CH$_3$ | 1 |
| 34 (B=H) | H | (2,3-dimethylphenyl)NH-SO$_2$-(3-substituted phenyl)-NH-C(=O)-CH$_2$-CH$_2$-NH-C(=O)-CH$_3$ | 0 |
| 35 (B=CH$_3$) | H | | |
| 36 (B=CH$_3$) | H | (2,3-dimethylphenyl)NH-SO$_2$-(3-substituted phenyl)-NH-C(=O)-CH$_2$-CH$_2$-NH-C(=O)-CH$_3$ | 1 |

TABLE 3-continued
(Ib')
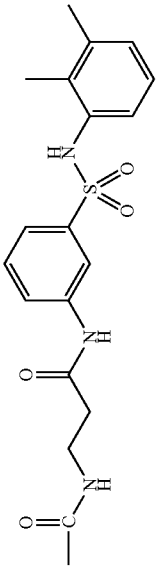
| Example | A | G₂ | n |
|---|---|---|---|
| 37 (B=CH₃) | H | 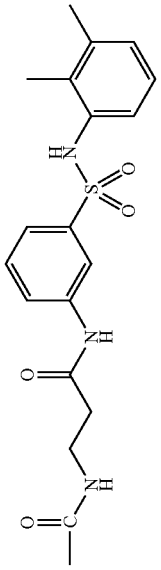 | 2 |
| 38 (B=H) 39 (B=CH₃) | CH₃ | 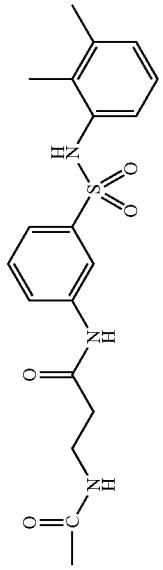 | 0 |
| 40 (B=H) 41 (B=CH₃) | CH₃ | 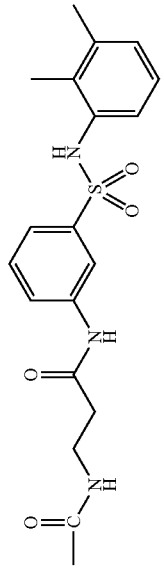 | 1 |
| 42 (B=H) 43 (B=CH₃) | CH₃ | 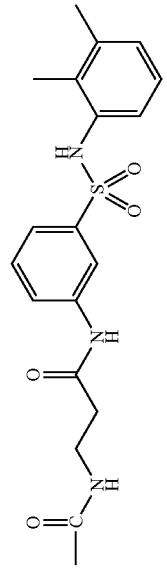 | 2 |
| 44 (B=H) 45 (B=CH₃) |  | 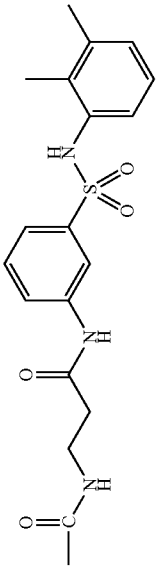 | 0 |

TABLE 3-continued (Ib')

| Example | A | G₂ | n |
|---|---|---|---|
| 46 (B=H) 47 (B=CH₃) | isoprenyl-CH— | 3-(2,3-dimethylphenylsulfamoyl)phenyl-NH-C(O)-CH₂-CH₂-NH-C(O)-CH₃ | 1 |
| 48 (B=H) | isoprenyl-CH— | 3-(2,3-dimethylphenylsulfamoyl)phenyl-NH-C(O)-CH₂-CH₂-NH-C(O)-CH₃ | 2 |
| 49 (B=H) | C₁₃H₂₇-CH₂— | 3-(2,3-dimethylphenylsulfamoyl)phenyl-NH-C(O)-CH₂-CH₂-NH-C(O)-CH₃ | 0 |
| 50 (B=H) | C₁₄H₂₉-CH₂— | 3-(2,3-dimethylphenylsulfamoyl)phenyl-NH-C(O)-CH₂-CH₂-NH-C(O)-CH₃ | 0 |

TABLE 3-continued
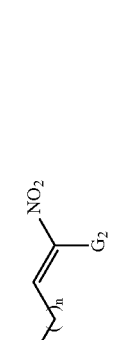

EXAMPLES 54-68

By use of the synthesis schemes described herein, the following compounds of Formula (I') could be prepared, as indicated in Table 4:

TABLE 4
$$\underset{G_1}{\overset{G_3}{>}}=\underset{G_2}{\overset{NO_2}{<}} \quad (I')$$
| Example | $G_1$ | $G_2$ | $G_3$ |
|---|---|---|---|
| 54 | 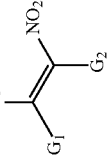 | H | CH$_3$ |
| 55 |  | CH$_3$ | CH$_3$ |
| 56 |  | ![structure] | CH$_3$ |
| 57 | 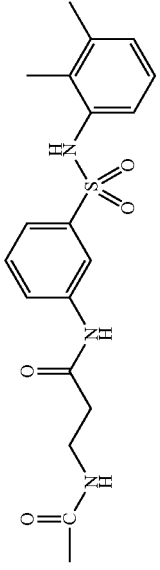 | H | CH$_3$ |
| 58 |  | CH$_3$ | CH$_3$ |
For Example 56, $G_2$ =

TABLE 4-continued
| Example | G₁ | G₂ | G₃ |
|---|---|---|---|
| 59 | 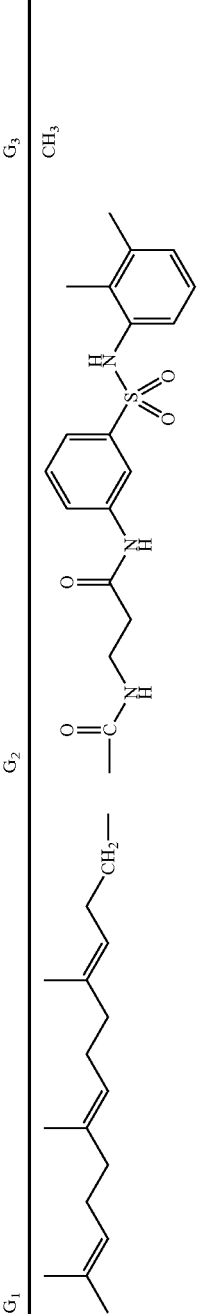 |  | CH₃ |
| 60 | 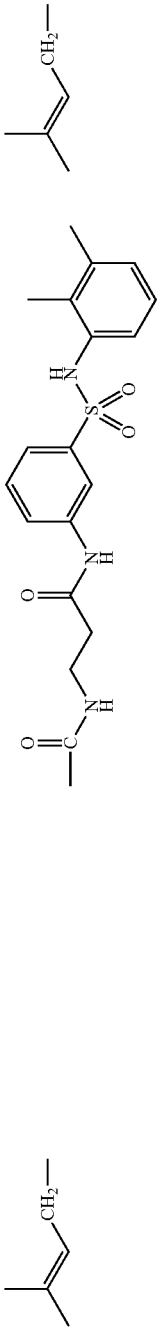 | H | 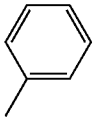 |
| 61 | 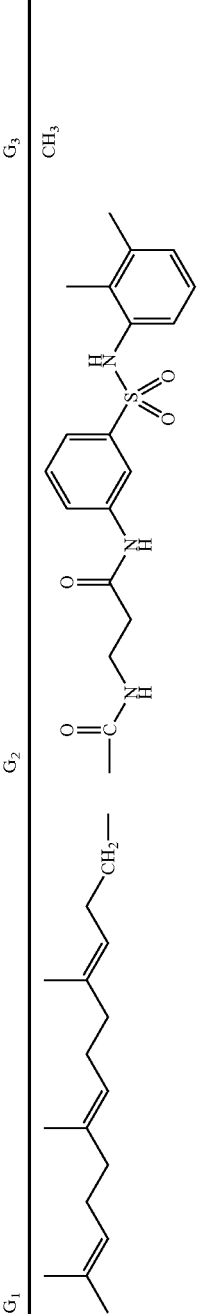 | CH₃ |  |
| 62 | 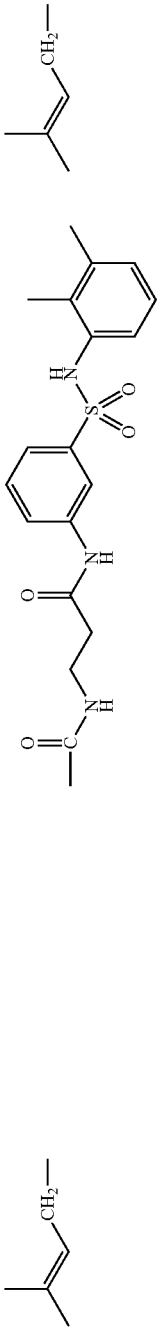 | 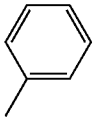 | 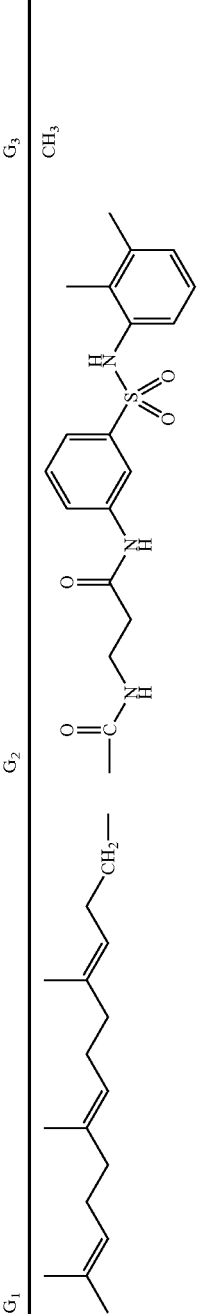 |
| 63 |  | H | 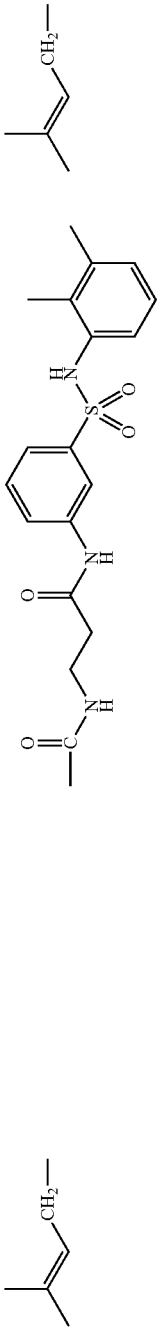 |

TABLE 4-continued $$\begin{array}{c} G_3 \\ | \\ G_1 \end{array} C = C \begin{array}{c} NO_2 \\ | \\ G_2 \end{array} \quad (I')$$

| Example | G₁ | G₂ | G₃ |
|---------|-----|-----|-----|
| 64 | —CH₂—(CH₂)₁₂—CH₃ | —CH₂—CH₃ | |
| 65 | —CH₂—(CH₂)₁₂—CH₃ | —CH₂—(CH₂)—C(O)NH—C₆H₄—S(O)₂NH—C₆H₃(CH₃)₂ | —C₆H₄—CH₃ |
| 66 | —CH₂—(CH₂)₇ | H | —CH₂—(CH₂)₇ |
| 67 | —CH₂—(CH₂)₇ | CH₃ | —CH₂—(CH₂)₇ |
| 68 | —CH₂—(CH₂)₇ | —CH₂—(CH₂)—C(O)NH—C₆H₄—S(O)₂NH—C₆H₃(CH₃)₂ | —CH₂—(CH₂)₇ |

While particular embodiments of the present invention have been described and illustrated, it should be understood that the invention is not limited thereto since modifications may be made by persons skilled in the art. The present application contemplates any and all modifications that fall within the spirit and scope of the underlying invention disclosed and claimed herein.

What is claimed is:

1. A method for the treatment of cancer in a patient, the method comprising administering an effective amount of a compound of Formula (I) to a patient in need thereof

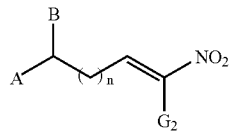

or pharmaceutically acceptable salt thereof, wherein:

A is

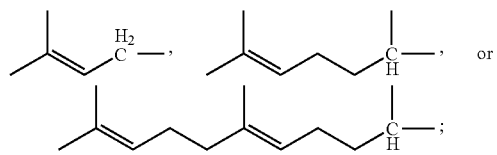

B and $G_2$ are independently hydrogen or methyl; and n is 0, 1, or 2.

2. The method of claim 1, wherein said compound of Formula (I) is selected from the group consisting of 5,9,13-trimethyl-2-nitrotetradeca-2,8,12-triene (RG-4); 4,8-dimethyl-1-nitronona-1,7-diene (RG-7); 5,9-dimethyl-2-nitrodeca-2,8-diene (RG-14); and their pharmaceutically acceptable salts.

3. A method for the treatment of cancer in a patient in need thereof, the method comprising administering an effective amount of a compound of Formula (I)

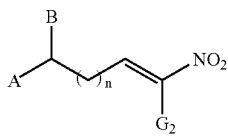

or pharmaceutically acceptable salt thereof, wherein:

A is hydrogen,

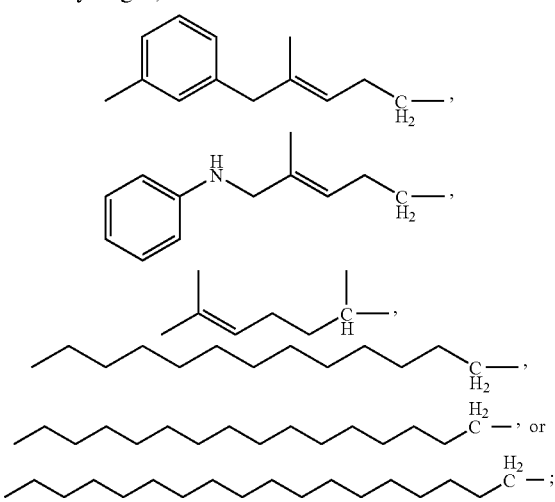

B is hydrogen or methyl;
$G_2$ is hydrogen, methyl, or

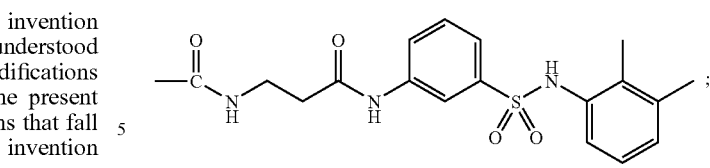

and
n is 0, 1, or 2.

4. A method for the treatment of cancer in a patient in need thereof, the method comprising administering an effective amount of a compound of Formula (I)

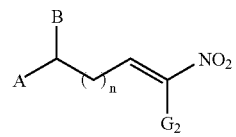

or pharmaceutically acceptable salt thereof, wherein:

A is hydrogen, methyl,

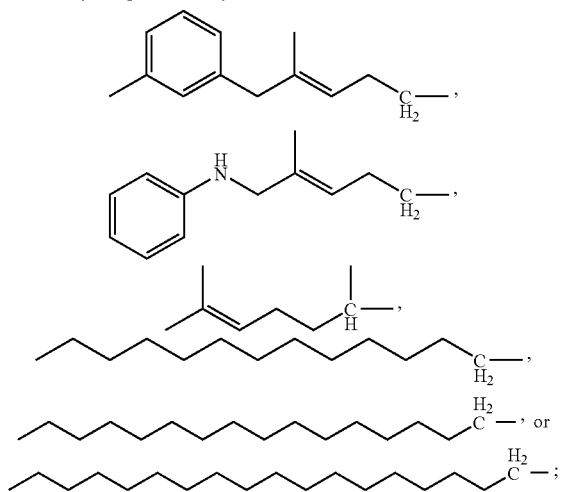

B is hydrogen;
$G_2$ is hydrogen, methyl, or

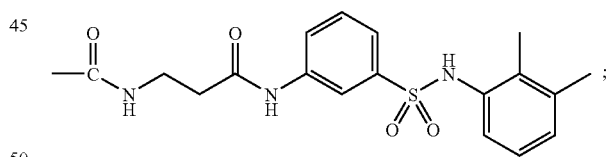

and
n is 0, 1, or 2.

5. A method for the treatment of cancer in a patient in need thereof, the method comprising administering an effective amount of a compound of Formula (I)

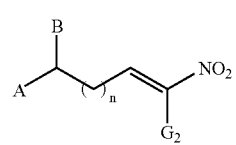

or pharmaceutically acceptable salt thereof, wherein:

A is hydrogen, methyl,

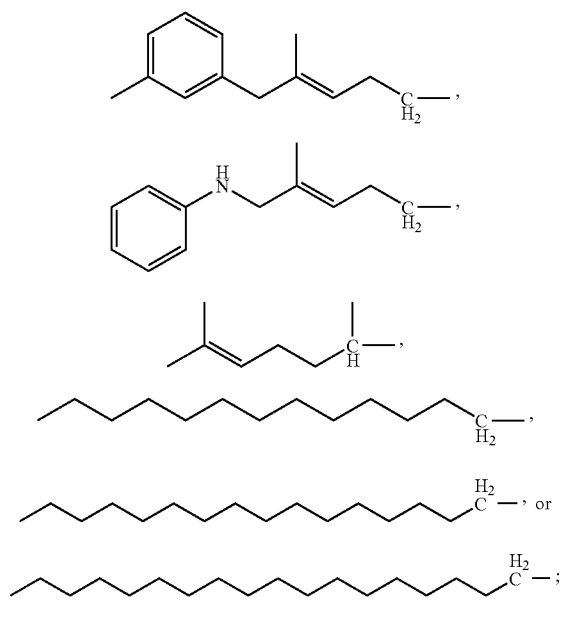
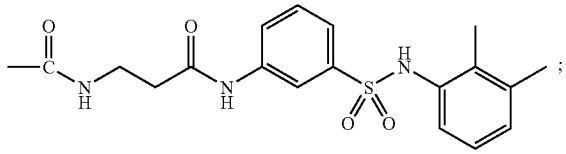
B is hydrogen or methyl;
G₂ is methyl or
and
n is 0, 1, or 2.
6. A method for the treatment of cancer in a patient in need thereof, the method comprising administering an effective amount of a compound of Formula
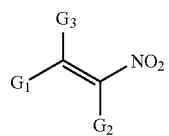
or pharmaceutically acceptable salt thereof, wherein:
G₁ is
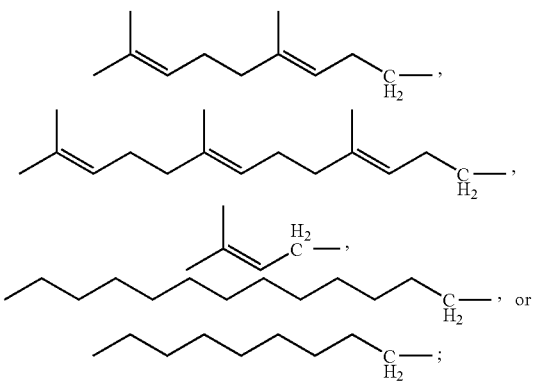
G₂ is hydrogen, methyl, or
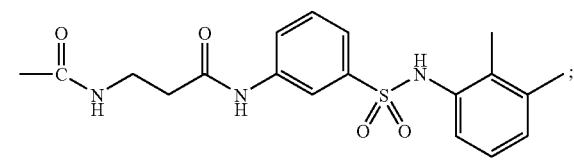
and
G₃ is methyl, phenyl,
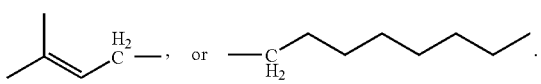
\* \* \* \* \*